(12) United States Patent
Ogawa

(10) Patent No.: US 6,609,425 B2
(45) Date of Patent: *Aug. 26, 2003

(54) ULTRASONIC PROBE AND ULTRASONIC DIAGNOSIS APPARATUS USING THE SAME

(75) Inventor: Eiji Ogawa, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/843,773

(22) Filed: Apr. 30, 2001

(65) Prior Publication Data

US 2001/0039836 A1 Nov. 15, 2001

(30) Foreign Application Priority Data

May 2, 2000 (JP) .......................... 2000-133084

(51) Int. Cl.[7] ............................ G01N 29/04; A61B 8/12
(52) U.S. Cl. ............................. 73/608; 73/620; 73/655; 73/646; 73/643; 600/447
(58) Field of Search .................... 73/608, 643, 655, 73/657, 656, 620; 356/352, 358; 600/447, 448

(56) References Cited

U.S. PATENT DOCUMENTS

| | | | | |
|---|---|---|---|---|
| 3,831,135 A | * | 8/1974 | Smith ............................ 73/608 |
| 4,006,627 A | * | 2/1977 | Bossaert ........................ 73/608 |
| 4,554,836 A | * | 11/1985 | Rudd ............................ 73/655 |
| 4,873,989 A | * | 10/1989 | Einzig ....................... 73/861.52 |
| 5,080,491 A | * | 1/1992 | Monchalin et al. ......... 356/352 |
| 5,103,676 A | * | 4/1992 | Garcia et al. ................. 73/597 |
| 5,305,756 A | * | 4/1994 | Entrekin et al. ............ 600/445 |
| 5,353,262 A | * | 10/1994 | Yakymyshyn et al. ........ 73/655 |
| 5,419,329 A | * | 5/1995 | Smith et al. ................. 600/447 |
| 5,450,752 A | * | 9/1995 | White et al. ................. 73/643 |
| 5,457,997 A | * | 10/1995 | Naruo et al. ................. 73/643 |
| 5,814,730 A | * | 9/1998 | Brodeur et al. ............... 73/597 |

* cited by examiner

Primary Examiner—Hezron Williams
Assistant Examiner—Jacques Saint-Surin
(74) Attorney, Agent, or Firm—Sughrue Mion, PLLC

(57) ABSTRACT

A two-dimensional ultrasonic probe has a transmitting function of an ultrasonic signal without electric interconnection of a numerous number of microcomponents and without increase in crosstalk and electric impedance. This probe includes an optical fiber array having a plurality of optical fibers to which light generated from a light source is made incident, a plurality of ultrasonic detecting elements, formed at one ends of the respective optical fibers, for modulating incident light via the optical fibers on the basis of the ultrasonic signal to be applied, and an ultrasonic transmitting element using a piezoelectric element.

21 Claims, 13 Drawing Sheets

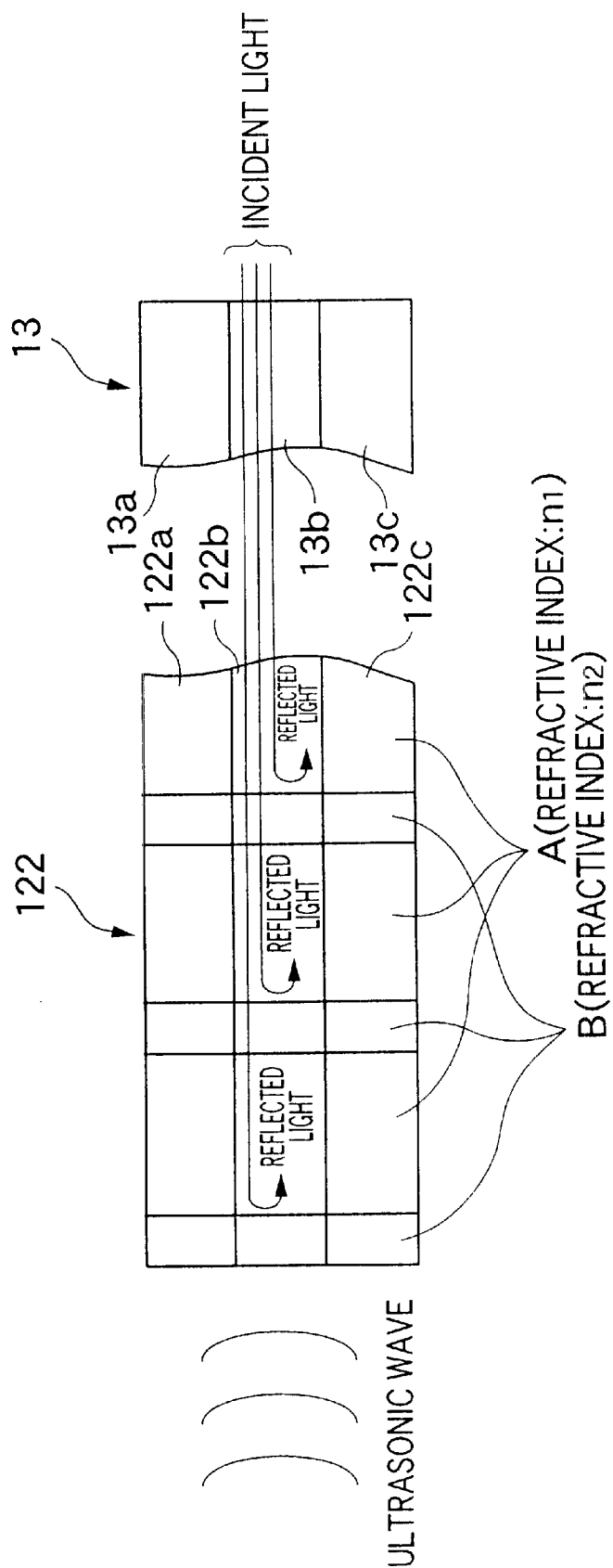

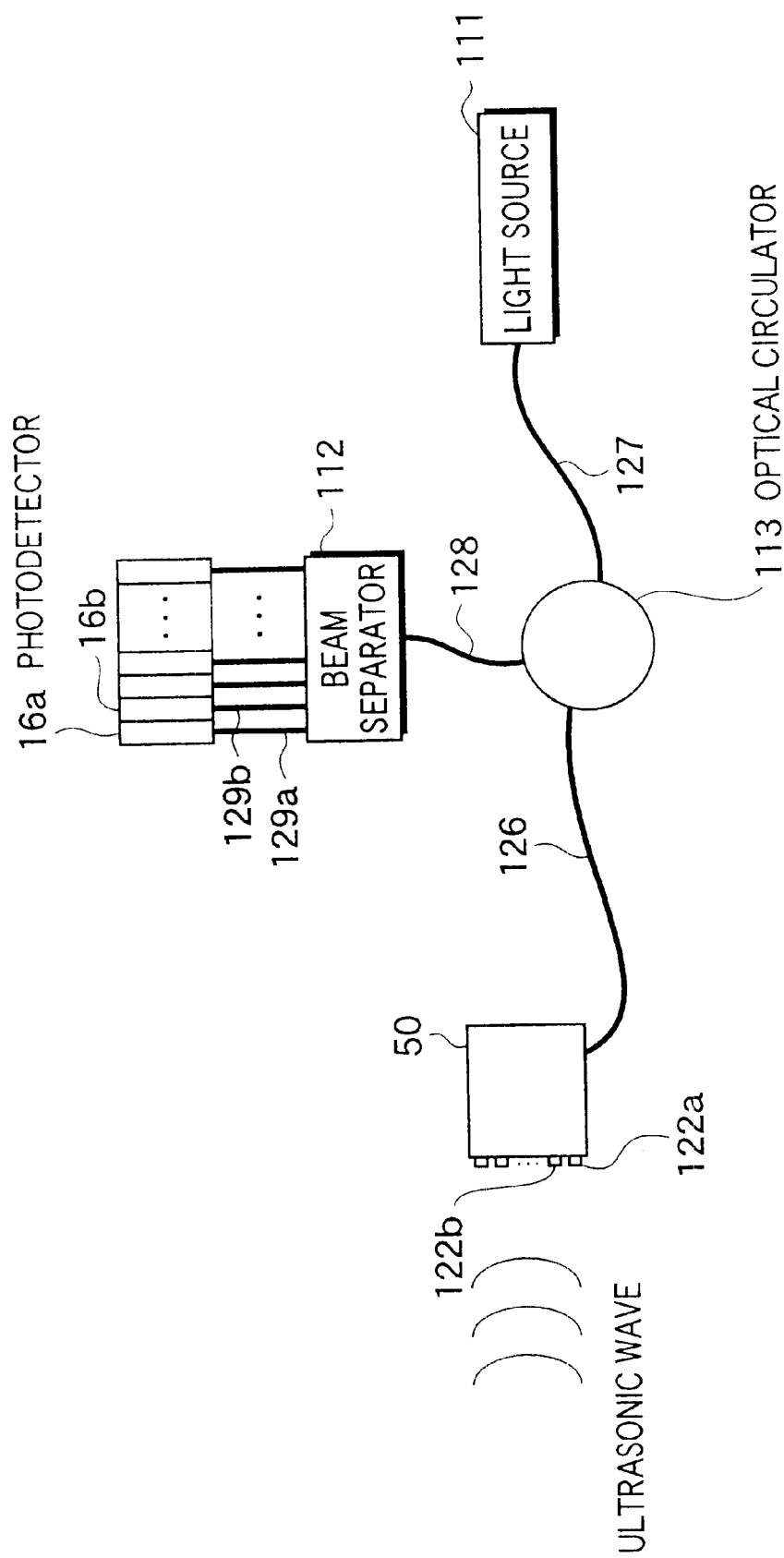

ULTRASONIC PROBE AND ULTRASONIC DIAGNOSIS APPARATUS USING THE SAME

BACKGROUND OF THE INVENTION

1. Field of the Invention

The present invention relates to a probe for receiving and transmitting an ultrasonic wave. Further, the present invention relates to an ultrasonic diagnosis apparatus for medical diagnosis by receiving and transmitting the ultrasonic wave with the probe.

2. Description of the Related Art

Hitherto, in ultrasonic diagnosis apparatuses, a single system has been used for receiving means and transmitting means of an ultrasonic wave. There among, as an element (vibrator) for receiving and transmitting the ultrasonic wave, one-dimensional sensor arrays are generally used. The one-dimensional sensor arrays employ piezoelectric materials such as piezoelectric ceramics represented by PZT (Pb (lead) zirconate titanate) or piezoelectric high-polymers represented by PVDF (polyvinyl difluoride). Further, a two-dimensional image is obtained by scanning the one-dimensional sensor array, and a plurality of the two-dimensional images are synthesized, thereby obtaining a three-dimensional image.

However, according to the above-mentioned technique, time lag is caused in the scan direction of the one-dimensional direction of the one-dimensional sensor array, and therefore, sectional images at different times are synthesized. As a consequence, the synthesized image becomes blurred. Therefore, in the case of ultrasonic echo observation using the ultrasonic diagnosis apparatus, this technique is not suitable for an object to be imaged such as a living organism.

In order to obtain the three-dimensional image using the ultrasonic wave with high quality, a two-dimensional sensor array is necessitated to obtain the two-dimensional image without scanning operation of the sensor array. Thus, a technique is examined to produce a two-dimensional sensor array by using the above-mentioned PZT or PVDF. The use of the PZT and PVDF needs the micro-fabrication of an element and the interconnection of a numerous number of microcomponents. However, the improvement in micro-fabrication and high-integration of the element is difficult under the present condition. If this improvement is realized, there are problems that crosstalk between elements will be increased, an SN ratio will be deteriorated by the rise in electric impedance due to fine interconnection, and an electrode portion of the fine element will be easily destroyed. Accordingly, the two-sensor array using the PZT or PVDF is hardly realized.

This results in desiring the employment of a two-dimensional sensor using optical fibers as an ultrasonic sensor using no piezoelectric material. However, the ultrasonic sensor using optical fibers has no transmitting function of the ultrasonic wave, and therefore, must have the transmission function.

SUMMARY OF THE INVENTION

Accordingly, the present invention is made in consideration of the above-discussed problems, and has its first object to provide a two-dimensional ultrasonic probe having a function for transmitting an ultrasonic signal without electric interconnection of a numerous number of microcomponents and without increase in crosstalk and electric impedance. Also, it is the second object to provide an ultrasonic diagnosis apparatus having the above-mentioned two-dimensional ultrasonic probe.

In order to overcome the problems, according to the present invention, an ultrasonic probe includes transmitting means for transmitting an ultrasonic signal and receiving means for receiving an ultrasonic signal, using a system different from that of the transmitting means.

According to the present invention, an ultrasonic diagnosis apparatus includes transmitting means for transmitting an ultrasonic signal, a drive signal generating circuit for generating a drive signal to be applied to the transmitting means so as to transmit the ultrasonic signal, receiving means for receiving an ultrasonic signal, using a system different from that of the transmitting means, a detector for detecting a reception signal supplied by the receiving means to generate a detection signal, signal processing means for processing the detection signal output from the detector, control means for controlling transmitting timing of the drive signal and receiving timing of the reception signal, an image processing unit for forming image data on the basis of an output signal of the signal processing means, and an image display unit for displaying an image on the basis of the image data.

According to the present invention, it is possible to realize a two-dimensional ultrasonic probe having a transmitting function of an ultrasonic signal without electric interconnection of a numerous number of microcomponents and without increase in crosstalk and electric impedance. Further, according to the present invention, it is possible to realize an ultrasonic diagnosis apparatus having the above-mentioned two-dimensional ultrasonic probe.

BRIEF DESCRIPTION OF THE DRAWINGS

FIG. 5 is a diagram showing partial structure of an ultrasonic probe according to a second embodiment of the present invention;

FIG. 11 is a diagram for explaining structure and operation of an ultrasonic probe according to a sixth embodiment of the present invention;

DESCRIPTION OF THE PREFERRED EMBODIMENTS

Figure 1:
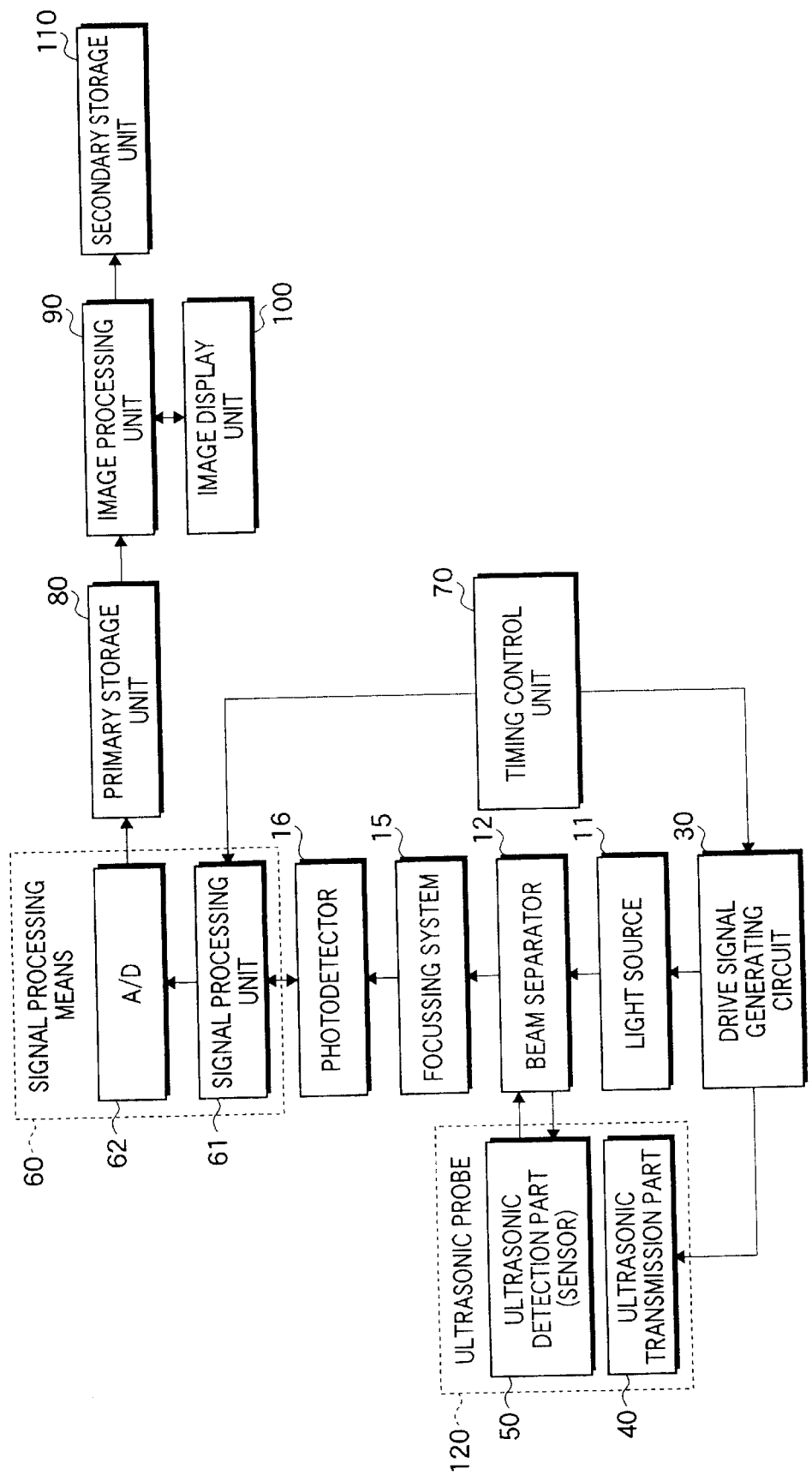
FIG. 1 is a block diagram showing an ultrasonic diagnosis apparatus using an ultrasonic probe according to a first embodiment of the present invention.

Embodiments of the present invention will be described in detail hereinbelow with reference to the drawings. Incidentally, the same reference numerals denote the same components and the description is omitted.

FIG. 1 is a block diagram showing an ultrasonic diagnosis apparatus using an ultrasonic probe according to a first embodiment of the present invention. As shown in FIG. 1, the ultrasonic diagnosis apparatus includes an ultrasonic probe 120 having an ultrasonic transmission part 40 and an ultrasonic detecting unit (sensor) 50. The ultrasonic transmission part 40 transmits an ultrasonic wave based on a drive signal which is generated by a drive signal generating circuit 30. The ultrasonic transmission part 40 comprises a vibrator using a piezoelectric element such as PZT or PVDF. The ultrasonic wave transmitted to a diagnosis target is reflected thereby, and the reflected ultrasonic wave is received by the ultrasonic detection part (sensor) 50. The sensor 50 includes an optical fiber array and an ultrasonic detecting element, etc.

Further, the ultrasonic diagnosis apparatus includes a light source 11, a beam separator 12, a focussing system 15, and a photodetector 16. The beam separator 12 may include a half mirror, an optical circulator, a polarizing beam splitter or the like. A detection signal output from the photodetector 16 is input to a signal processing unit 61 included in the signal processing means 60. Further, an output signal of the signal processing unit 61 is converted into a digital signal by an A/D converter 62.

A primary storage unit 80 is connected to the A/D converter 62, and a plurality of obtained planer data is stored in the primary storage unit 80. Based on the data, an image processing unit 90 reconstructs two-dimensional data or three-dimensional data. The reconstructed data is subjected to processes such as interpolation, response modulation, and gradation, and is displayed onto an image display unit 100. Further, the data processed by the image processing unit 90 is stored in a secondary storage unit 110.

A timing control unit 70 controls the drive signal generating circuit 30 to generate a drive signal at predetermined timing, and also controls the signal processing unit 61 to fetch the detection signal output from the photodetector 16 after a predetermined time passes from the transmission time. Thus, by controlling the drive signal and the detection signal, it is possible to limit a read-out time and to optically detect the reflection of the ultrasonic wave from a specific depth of an object to be photographed.

Figure 2:
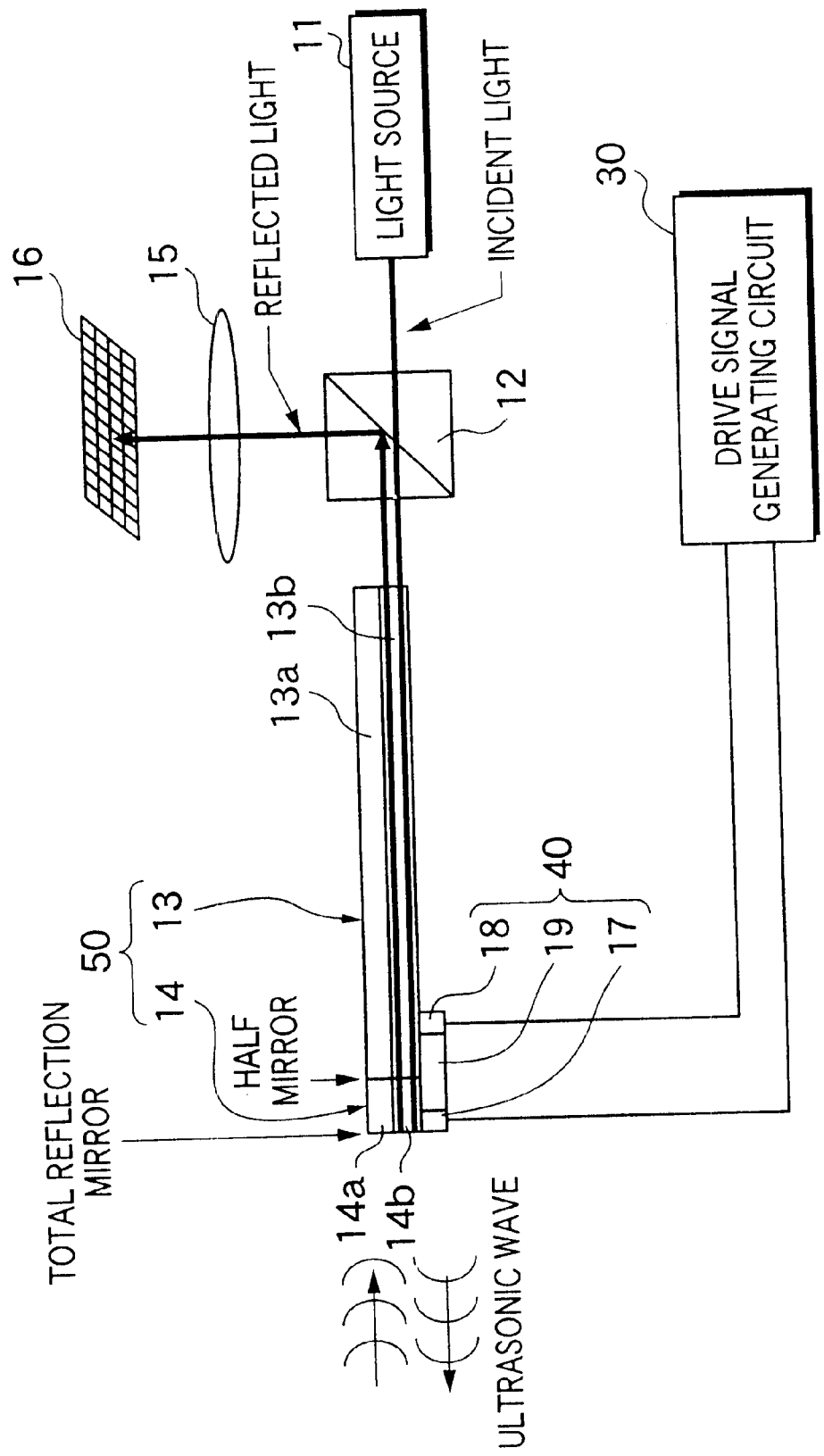
FIG. 2 is a diagram for explaining structure and operation of the ultrasonic probe according to the first embodiment of the present invention.

Next, a description will be given of the structure and operation of the ultrasonic probe as shown in FIG. 1 with reference to FIG. 2. As shown in FIG. 2, the ultrasonic probe comprises the ultrasonic transmission part 40 including an ultrasonic transmitting element (PZT, etc.) 19 with electrodes 17 and 18, and the ultrasonic detection part 50 including an ultrasonic detecting element 14 and an optical fiber array 13. The optical fiber array 13 is formed by arraying sectional planes of fine optical fibers 13a, 13b, ... in a two-dimensional matrix form.

The ultrasonic transmitting element 19 is made of at least one piezoelectric material such as a piezoelectric ceramic represented by PZT (Pb (lead) zirconate titanate) or a piezoelectric high-polymer represented by PVDF (polyvinyl difluoride). A voltage is applied between the electrodes 17 and 18 arranged at both ends of the ultrasonic transmitting element 19, then, a fine mechanical vibration is generated in the piezoelectric element, and the vibration is transmitted to a propagation medium adjacent to the piezoelectric element. Therefore, the drive signal generating circuit 30 supplies an electric signal as a pulse or an electric signal as a continuous wave to the electrodes 17 and 18, then, the voltage is applied to the piezoelectric element so that an ultrasonic pulse or continuous ultrasonic wave is generated and transmitted in the propagation medium as an ultrasonic beam.

The ultrasonic detecting element 14 provided at one end of the ultrasonic probe comprises Fabry-Perot-resonators (abbreviated as FPRs) 14a, 14b, ... as ultrasonic sensing parts formed at ends of the optical fibers, respectively. Light generated from the light source 11 passes through the beam separator 12 and is incident into the optical fiber array 13. The incident light of each of the optical fibers is reflected by a half mirror (at the right in the figure) and a total-reflection mirror (at the left in the figure) which are formed at both ends of the FPR. The total-reflection plane is geometrically displaced by the ultrasonic wave which has been transmitted by the piezoelectric element 19, reflected by the object and applied to the ultrasonic detecting element 14. As a result, the reflected light is modulated and then incident into the beam separator 12 again. The reflected light incident into the beam separator 12 is focused on a photodetector 16, which includes a CCD, a photodiode (PD) array or the like, directly or through an optical fiber or through a focussing system 15 such as a lens.

Figure 3:
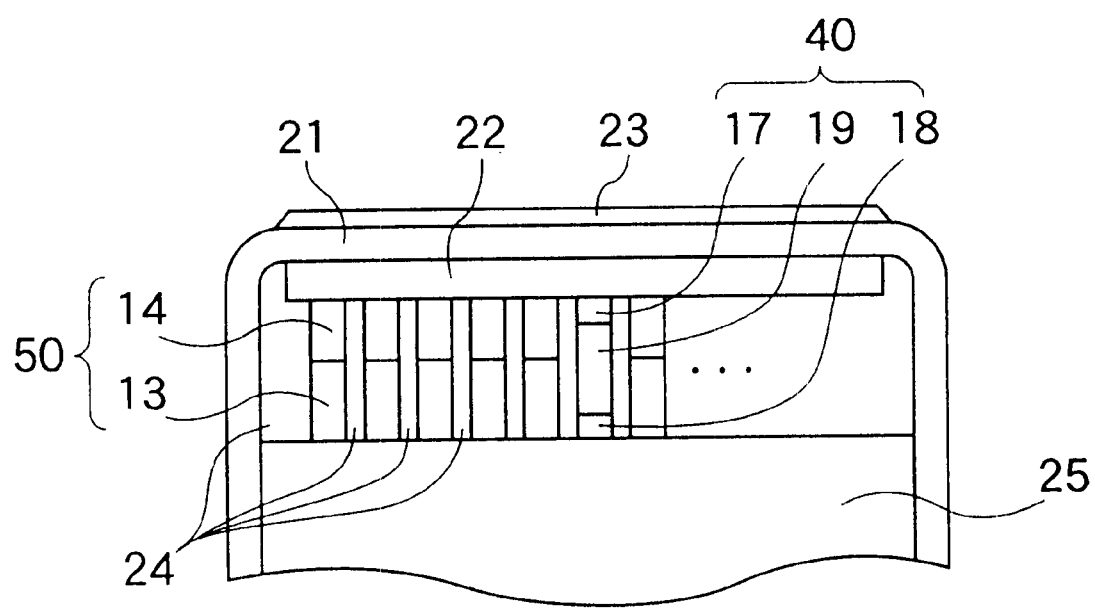
FIG. 3 is a diagram showing partial structure of the ultrasonic probe according to the first embodiment of the present invention.

The structure of the above-mentioned ultrasonic probe will be specifically described with reference to FIGS. 3 and 4. As shown in FIG. 3, at least one ultrasonic transmission part 40 including an ultrasonic transmitting element 19 with electrodes 17 and 18, and a plurality of ultrasonic detection part 50 each including an ultrasonic detecting element 14 and an optical fiber array 13 are enclosed in a housing 21. Preferably, an interval between the optical fibers is equal to or less than a half wavelength of the ultrasonic wave to be received so as to suppress a side lobe.

Preferably, an acoustic matching layer 22 is provided between the ultrasonic detecting element 14 and ultrasonic transmitting element 19 and the housing 21 so as to match acoustic impedance. The acoustic matching layer 22 may be made of a material, which easily transmits the ultrasonic wave, such as Pyrex glass or epoxy resin including metal powder. Preferably, an acoustic lens member 23 made of, for example, silicone rubber is provided onto the surface of the housing 21. The acoustic lens member 23 also serves to protect the ultrasonic detecting element 14 and the ultrasonic transmitting element 19. Further, preferably, a space between the optical fibers and the ultrasonic transmitting element is filled with a sound absorbing material 24 so as to decrease crosstalk of the ultrasonic wave. Epoxy resin including metal powder and rubber including ferrite powder, etc. are suitable as the sound absorbing material 24. Incidentally, the optical fiber array 13 is solidified with resin 25, except for a portion near which the ultrasonic detecting element 14 is provided therein.

The four following examples of the arrangement of the optical fiber 13, to which the ultrasonic detecting element 14 is provided, and the ultrasonic receiving element 19 are proposed as shown in FIGS. 4A to 4D.

Figure 4A:
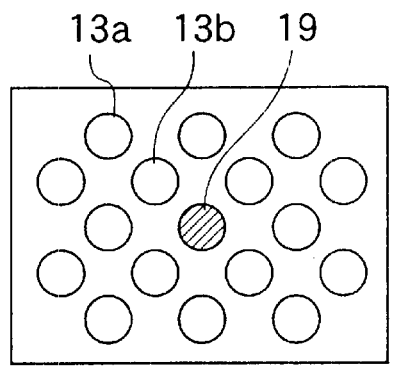
FIGS. 4A to 4D are diagrams showing partial structure of the ultrasonic probe according to the first embodiment of the present invention.

(1) An Example in Which One Ultrasonic Transmitting Element is Arranged at the Center of the Optical Fiber Array FIG. 4A is a cross-sectional view showing an example in which one ultrasonic transmitting element 19 is arranged at the center of the optical fiber array comprising the optical fibers 13a, 13b, . . . In this arrangement, a transmission wave is non-directional.

Figure 4B:
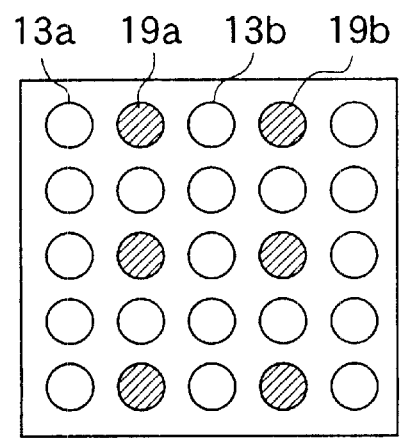

(2) An Example in Which a Plurality of Ultrasonic Transmitting Elements are Arranged Among a Plurality of Optical Fibers FIG. 4B is a cross-sectional view showing an example in which ultrasonic transmitting element 19a, 19b, . . . are alternately arranged among the optical fibers 13a, 13b, . . . constituting the optical fiber array. In this arrangement, the ultrasonic transmitting elements are two-dimensionally arranged, thereby enabling two-dimensional wave-transmission in beam scanning.

Figure 4C:
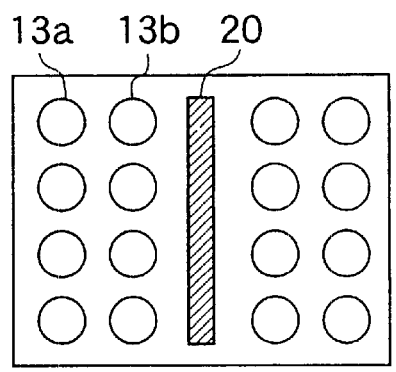

(3) An Example in Which One One-dimensional Transmitting Array is Arranged at the Center of the Optical Fiber Array FIG. 4C is a cross-sectional view showing an example in which one one-dimensional transmitting array 20 constituted by one-dimensionally arraying a plurality of ultrasonic transmitting elements is arranged among the optical fibers 13a, 13b, . . . constituting the optical fiber array. In the arrangement, one-dimensional wave-transmission in beam scanning is possible.

Figure 4D:
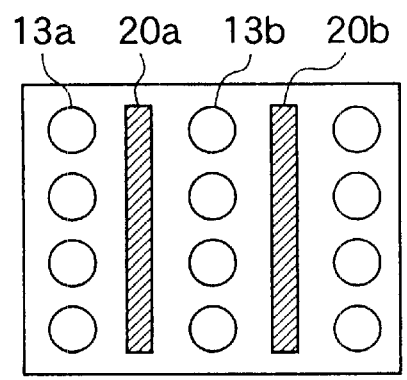

(4) An Example in Which a Plurality of One-dimensional Arrays are Arranged Among a Plurality of Optical Fibers FIG. 4D is a cross-sectional view showing an example in which one-dimensional transmitting arrays 20a, 20b, . . . constituted by one-dimensionally arraying a plurality of ultrasonic transmitting elements are alternately arranged among the optical fibers 13a, 13b, . . . constituting the optical fiber array. In the arrangement, two-dimensional wave-transmission in beam scanning is possible.

Referring now to FIG. 5, an ultrasonic probe according to a second embodiment of the present invention will be described. FIG. 5 is a diagram for illustratively showing a basic idea of a portion of the above-described ultrasonic probe according to the second embodiment of the present invention. In this ultrasonic probe, a fiber Bragg grating is employed, instead of the Fabry-Perot-resonators provided in the first embodiment. That is, in the second embodiment, a Bragg grating portion 122 having a Bragg grating structure is provided as an ultrasonic sensing part at a tip portion of an optical fiber array 13 which is the same as the optical fiber array shown in FIG. 1. Precisely speaking, the ultrasonic detecting element 122 is constituted by such Bragg grating portions 122a, 122b, . . . which are formed at the respective tip portions of optical fibers 13a, 13b, . . .

A Bragg grating portion is arranged by two sorts of material layers (light propagatable medium) having different refractive indexes in such a manner that several thousands of these material layers are alternately overlapped with each other in such a pitch capable of satisfying the Bragg's reflection condition. This Bragg grating portion can have a higher reflectance factor, and a sharper wavelength dependent characteristic, as compared with those of a single layer Fabry-Perot-resonator. In FIG. 5, there are shown a material layer A having a refractive index "$n_1$", and a material layer B having another refractive index "$n_2$". Assuming now that a pitch (interval) of a periodic structure of these material layers is equal to "d", and also a wavelength of incident light is equal to "$\lambda$", the Bragg's reflection condition is expressed by the following formula (1). Note that symbol "m" indicates an arbitrarily-selected integer:

$$2d \cdot \sin\theta = m\lambda \tag{1}$$

where symbol "$\theta$" denotes an incident angle measured from a light-entering plane. Assuming now that $\theta = \pi/2$, the below-mentioned formula (2) is given:

$$2d = m\lambda \tag{2}$$

A Bragg grating may selectively reflect such light having a specific wavelength capable of satisfying the Bragg's reflection condition, whereas light having other wavelengths may pass through this Bragg grating.

When ultrasonic waves are propagated to the Bragg grating portion, the Bragg grating portion is distorted, so that the pitch "d" of the above-described periodic structure is changed. As a result, the wavelength "$\lambda$" of the selectively reflected light is changed. In the reflection characteristic of the Bragg grating, there are inclined bands where reflectance factors are changed, which are positioned before/after a center wavelength of light having the highest reflectance factor (low transmittance). While detection light having a center wavelength within a range of the inclined bands is entered into the Bragg grating portion, the ultrasonic waves are applied thereto. As a result, a change in intensity of reflection light (otherwise transmission light) in response to strengths of ultrasonic waves can be monitored. The strengths of ultrasonic waves can be measured by converting this change in the intensity of this light.

In this case, generally speaking, Bragg gratings may be easily manufactured while having high sensitivities, and therefore, commercially available Bragg grating products may be alternatively employed. However, these commercially available Bragg grating products cannot be directly used as high sensitive sensors in ultrasonic diagnostic purposes. For example, when a Brag grating used in this market is employed, such a confirmation can be made. That is, in a frequency band higher than 20 kHz, a sensitivity of this Bragg grating with respect to ultrasonic waves entered along an axial direction would be lowered. Also, in the case that a length of an ultrasonic sensing part (Bragg grating portion) is longer than approximately ¾ of a wavelength of an ultrasonic wave entered to the Bragg grating portion, a detected waveform is distorted on the side of the low frequency band, as compared with the waveform of the actually received ultrasonic wave, and the sensor sensitivity is lowered. This ultrasonic wavelength is expressed as follows:

(ultrasonic wavelength)=(sound velocity in Bragg grating portion)/ (frequency of ultrasonic wave)

These waveform distortion and lowering of sensor sensitivity may be conceived by the following reasons: In such a case that the length of the Bragg grating portion is longer than a half of the ultrasonic wave wavelength in the Bragg grating portion, while the ultrasonic wave is propagated through the Bragg grating portion, such a portion that expand/compress phases are inverted is produced in the Bragg grating portion. As a result, displacement of these portions is canceled.

To avoid an occurrence of such a phenomenon, a length of a Bragg grating portion may be selected to be shorter than, or equal to approximately ¾ of an ultrasonic wavelength, preferably to be equal to an approximately half of this ultrasonic wavelength. For instance, in such a case that a frequency of an ultrasonic wave to be detected is selected to be 3.5 MHz, and a sound velocity within a material of a Bragg grating portion is equal to 5,500 m/s, a wavelength "$\lambda_s$" of an ultrasonic wave which is propagated through the Bragg grating portion may be calculated as follows:

$\lambda_s = 5500/(3.5 \times 10^6) = 1571.4$ (micrometers).

As a result, an upper limit length of the Bragg grating portion may be calculated as follows:

1571×(¾)=1178.5 (micrometers).

As a result, if a length of such a Bragg grating portion is shorter than, or equal to 1178.5 micrometers, then it is possible to prevent inversion of expand/compress phases occurred in the Bragg grating portion, and also possible to obtain sensitivities required to detect ultrasonic waves.

Figure 6:
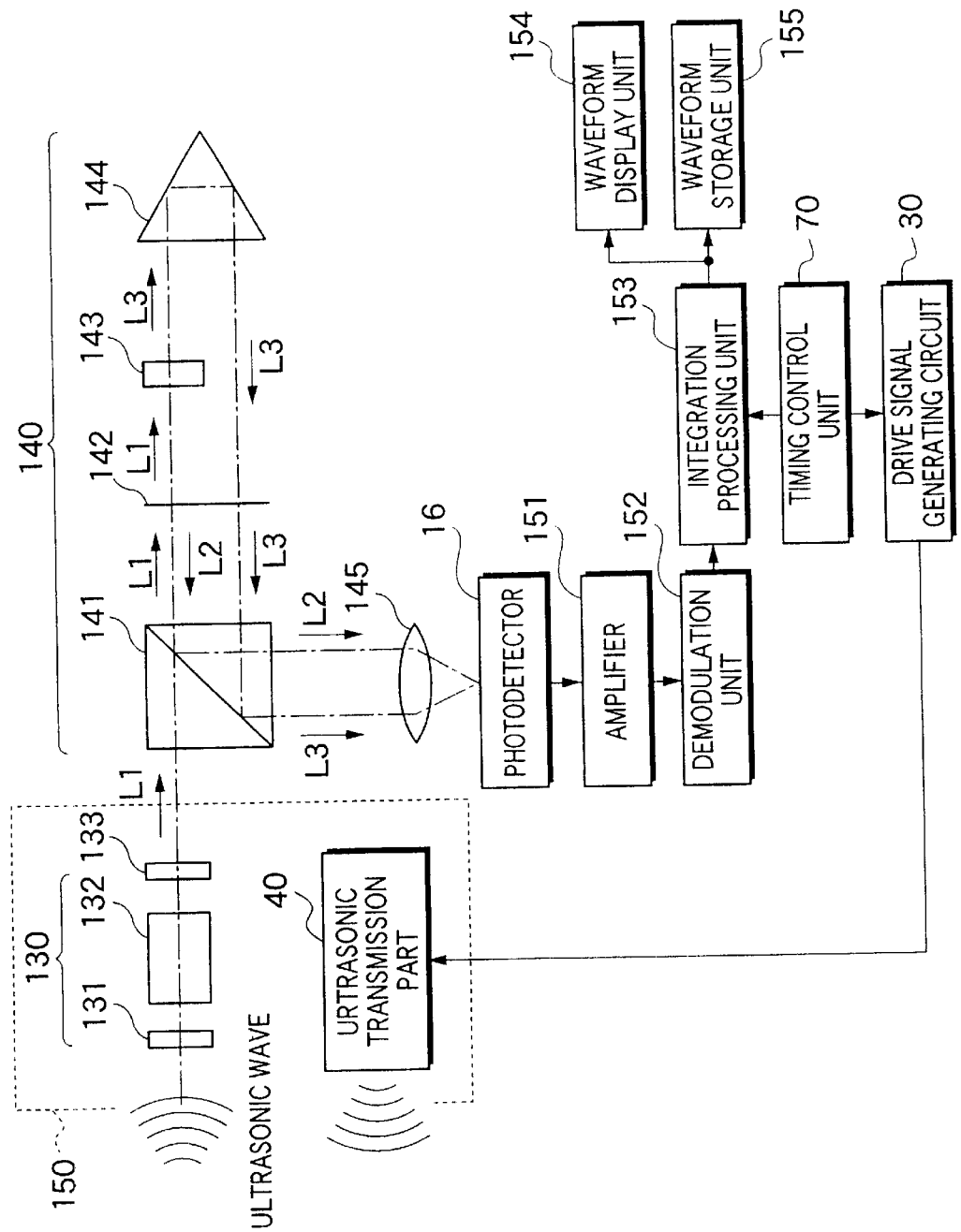
FIG. 6 is a diagram for explaining structure and operation of an ultrasonic probe according to a third embodiment of the present invention.

Next, an ultrasonic probe according to a third embodiment of the present invention will be described with reference to FIG. 6. As shown in FIG. 6, an ultrasonic probe 150 incorporates an ultrasonic transmission part 40 and an ultrasonic detecting unit 130 using a laser resonator for providing emission light whose frequency is changed by receiving an ultrasonic wave to an optical heterodyne interference optical system having different lengths of optical paths. A timing control unit 70 controls a drive signal generating circuit 30 to generate a drive signal at predetermined timing, and also controls integrating processing means 153 to fetch a detection signal output from a photodetector 16 via an amplifier 151 and demodulation unit 152 after a predetermined time passes from the transmission time.

In response to an output signal from the drive signal generating circuit 30, the ultrasonic transmission part 40 comprising a piezoelectric element such as a PZT generates an ultrasonic wave. The ultrasonic wave, which has been transmitted by the ultrasonic transmission part 40 and reflected by an object to be imaged, is incident to an incident plane (at the left of a total-reflection mirror 131). Then, the total-reflection mirror 131 of the laser resonator constituting the ultrasonic detecting unit 130 is displaced, and an interval between the total-reflection mirror 131 and a transparent mirror 133 is changed. As a result, the number of vibrations of a stationary wave, i.e., a resonance frequency is changed which is generated between two mirrors set on both sides of a laser activating material 132. Thus, an oscillation frequency of the laser shifts. A difference of lengths of optical paths is caused in the interference optical system 140 between a light beam L2 and a light beam L3. The light beam L2 passes through a beam separator 141, and then, the light beam L2 is reflected by a partial reflection mirror 142 and the beam separator 141 to be input to the photodetector 16 via a lens 145. The light beam L3 passes through the partial reflection mirror 142, a frequency shifter 143 and a prism 144, the partial reflection mirror 142 again, and then, the light beam L3 is reflected by the beam separator 141 to be input to the photodetector 16 via the lens 145.

Herein, the light beam whose oscillation frequency shifts with elapsed time enters to the optical heterodyne interference optical system having the difference of the optical path lengths. Then, there is generated a beat signal having a frequency which shifts by a change amount of an oscillation frequency corresponding to time delay due to the difference of the optical path lengths, with a center frequency of an optical heterodyne interference signal in the previous state. The amplifier 151 amplifies the beat signal whose frequency is modulated, the demodulating unit 152 demodulates the amplified signal, and the integration processing unit 153 integrates the demodulated signal. Thus, change in frequencies, namely, a waveform of the ultrasonic wave can be reproduced. The waveform is displayed in a waveform display unit 154, and is simultaneously stored in a waveform storage unit 155. Based on that, image data of the object can be formed.

Figure 7:
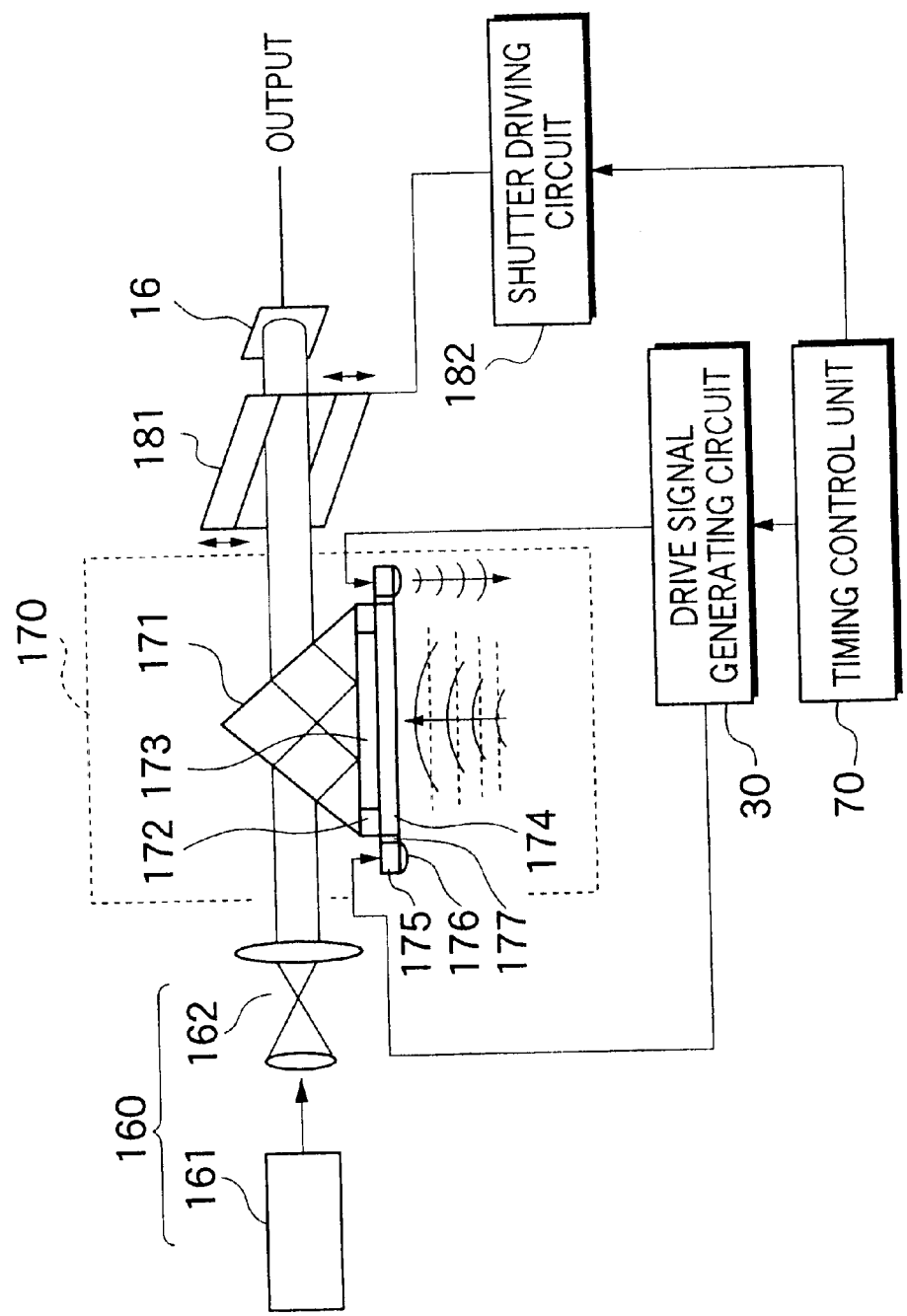
FIG. 7 is a diagram for explaining structure and operation of an ultrasonic probe according to a fourth embodiment of the present invention.

Further, a description is given of an ultrasonic probe according to a fourth embodiment of the present invention hereinbelow with reference to FIG. 7. As shown in FIG. 7, an ultrasonic probe 170 incorporates an ultrasonic transducer using a technique that an object existing in an evanescent field receiving an ultrasonic wave vibrates, and thereby, the light amount of evanescent light changes.

The ultrasonic transducer comprises a prism 171, an air gap portion 173, an optical flat 174 and a spacer 172 for forming a space where components 171–174 serve as receiving means, and a piezoelectric element 175, such as a PZT, provided to the optical flat 174 via a sound absorbing layer 177 and an acoustic lens 176 where components 175 and 176 serve as transmitting means.

A bottom of the prism 171 is irradiated with expanded laser beams emitted from the light source 160 comprising a laser resonator 161 and a beam expander 162. The photodetector 16 comprising a PD array or a CCD camera reads out the intensity distribution of the total reflected lights. On the other hand, when the ultrasonic wave transmitted by the piezoelectric element 175 is reflected by the object and is made incident from the lower surface of the optical flat 174, the thickness of an air gap portion 173 is changed. In accordance therewith, light leaked to the evanescent field at the lower surface of the prism 171, in other words, the light amount of evanescent light is changed. The light amount of the total reflected light read by the photodetector 16 is given bellow.

(Light amount of total reflected light)=(light amount of incident light)−(light amount of evanescent light)

Therefore, the intensity distribution of total reflected light expresses the change in pressure of an air layer in the evanescent filed, that is, the distribution of sound pressures of the ultrasonic waves. A signal read by the photodetector 16 is output to the signal processing unit.

A timing control unit 70 controls a drive signal generating circuit 30 to generate a drive signal at a predetermined timing, and also controls a timing of light (detection light) incident upon the photodetector 16. In order to control a timing of the light incident upon the photodetector 16, it is considered to drive a laser beam by a pulse or to provide a shutter or the like in the optical path to cut off the detection light. In the present embodiment, the reflected light at the bottom of the prism 171 is controlled to be incident upon the photodetector 16. The timing control unit 70 controls a shutter driving circuit 182 for driving a shutter 181. By limiting a time period within which the total reflected light depending on the intensity of ultrasonic waves is made incident upon the detector, it is possible to optically detect the reflection of the ultrasonic wave from the specific depth of the object. In this case, the shutter is opened or closed with a time delay from transmission of the ultrasonic wave in order to collect information of arbitrary depth in the object. Based on the thus-obtained detection signal, the image data of the object can be formed.

Figure 8:
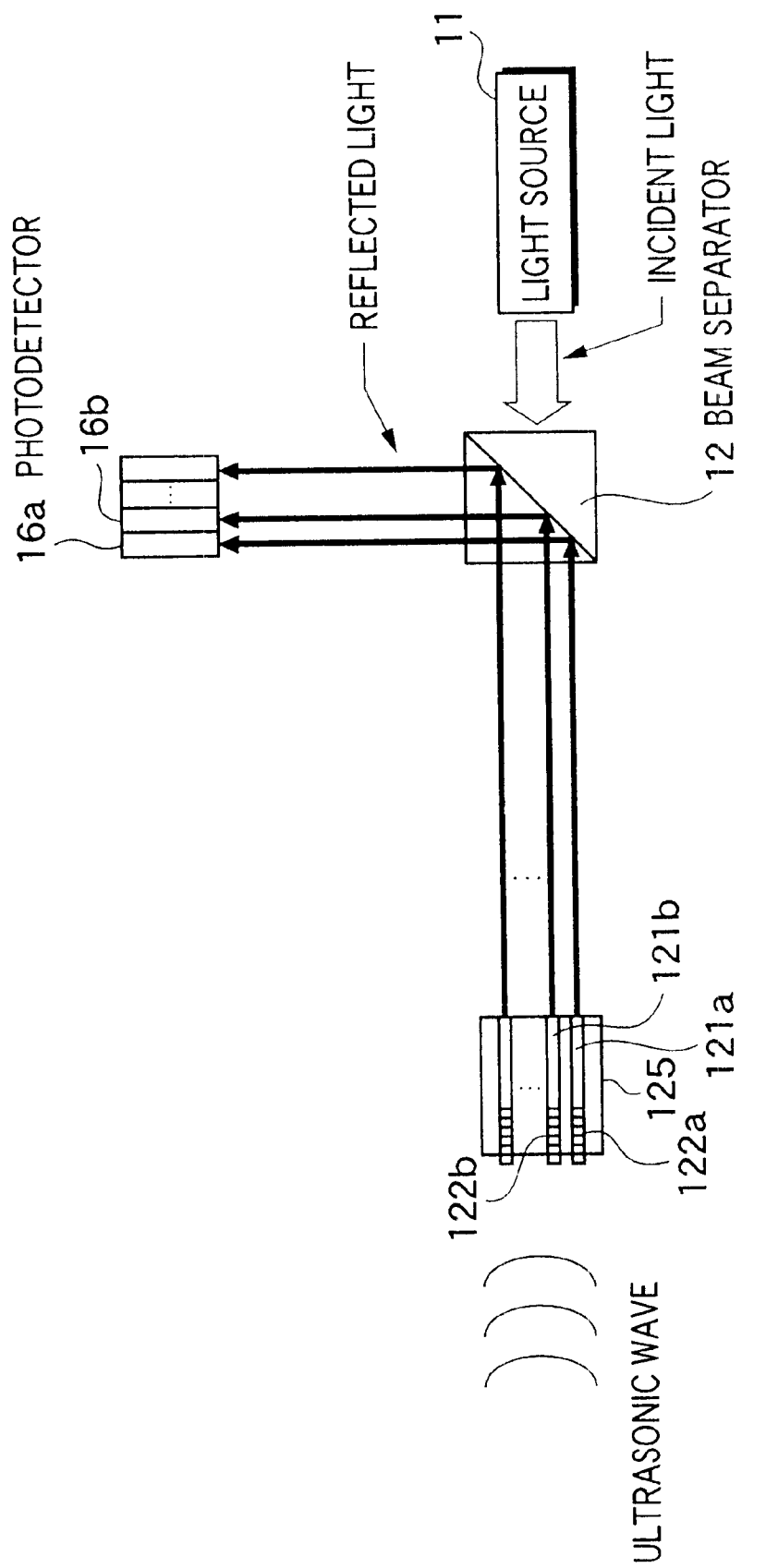
FIG. 8 is a diagram for explaining structure and operation of an ultrasonic probe according to a fifth embodiment of the present invention.

Next, an ultrasonic receiving apparatus according to a fifth embodiment of the present invention will now be described with reference to FIG. 8. This fifth embodiment is featured by that an optical waveguide path having a Bragg grating structure is employed as an ultrasonic wave detecting element. As indicated in FIG. 8, a plurality of optical waveguide paths 121a, 121b, . . . which are arranged in a one-dimensional array are formed on a board 125. Further, Bragg grating portions 122a, 122b, . . . are formed on core tip portions of these optical waveguide paths, respectively. The structure of the Bragg grating portion is similar to that of the ultrasonic probe according to the second embodiment of the present invention.

Light emitted from a light source 11 passes through a beam separator (optical demultiplexer) 12 and then the separated light is entered into the respective optical waveguide paths 121a, 121b, . . . In each of the respective optical waveguide paths, the Bragg grating portion formed at the tip portion thereof is changed in the structural aspect due to the propagation of the ultrasonic wave, so that the light is modulated. In each of the optical waveguide paths, the travel path of the light which is reflected by the Bragg grating portion is changed in the beam separator 12, and then the reflected light is entered into photodetectors 16a, 16b, . . . corresponding to the respective optical waveguide paths 121a, 121b, . . . As explained above, since changes in light intensity are detected by the photodetectors 16a, 16b, . . . strengths of ultrasonic waves which are propagated through the corresponding optical waveguide paths can be measured. It should be understood that similar to the second embodiment, in this fifth embodiment, a length of a Bragg grating portion formed on an optical waveguide path is preferably made shorter than, or equal to ¾ of a wavelength of an ultrasonic wave propagated through this Bragg grating portion.

Figure 9:
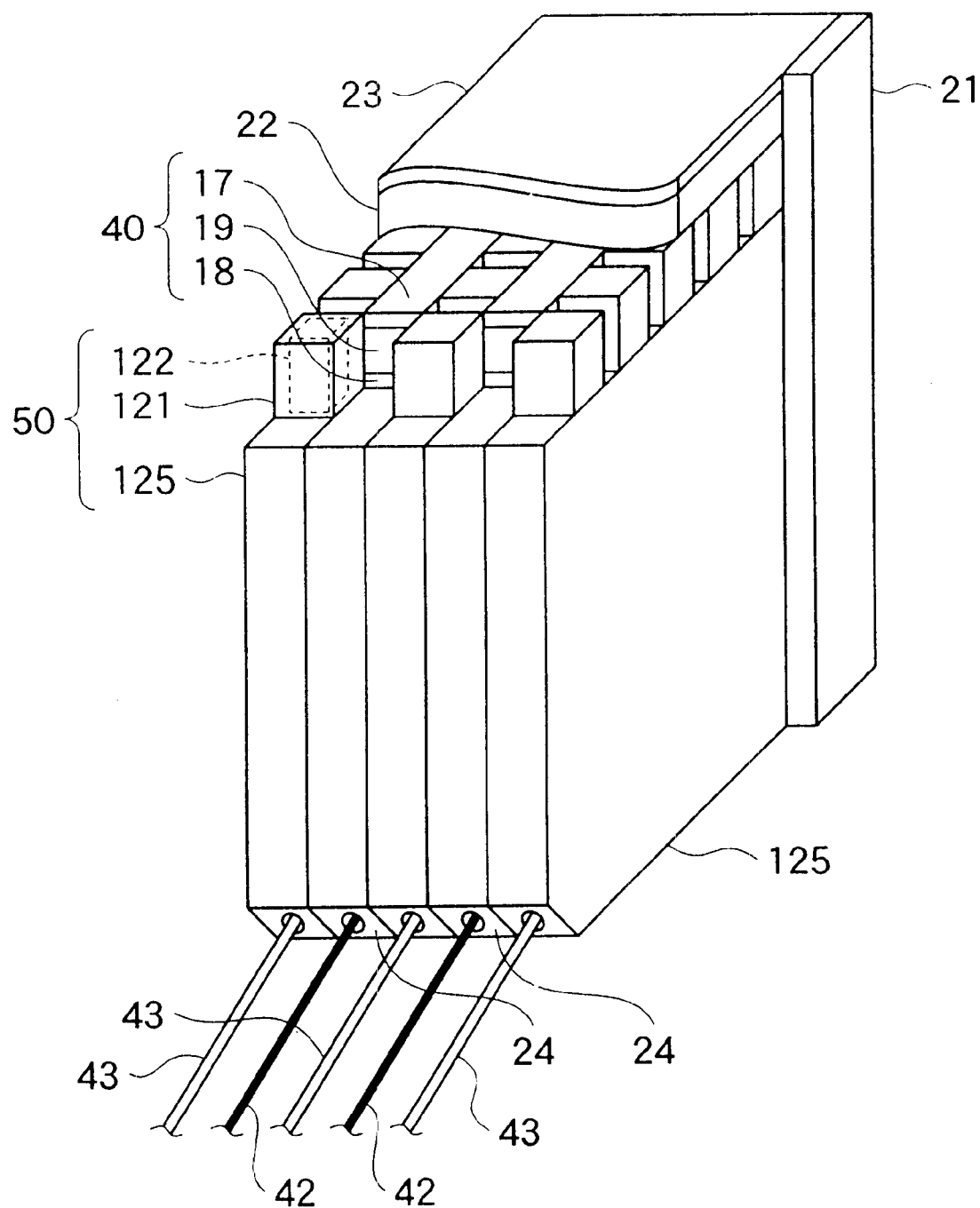
FIG. 9 is a diagram showing partial structure of the ultrasonic probe according to the fifth embodiment of the present invention.

FIG. 9 illustratively indicates a structure of a two-dimensional ultrasonic probe containing an optical waveguide path where a Bragg grating portion is formed. As indicated in FIG. 9, an ultrasonic detecting unit 50 and an ultrasonic transmission unit 40 are stored in a housing 21. The ultrasonic detecting unit 50 contains a plurality of optical waveguide paths 121a, 121b, . . . which are arranged in the one-dimensional manner on the board 125. The ultrasonic transmission unit 40 contains an ultrasonic transmitting element 19. In the ultrasonic detecting unit 50, the Bragg grating portions 122a, 122b, . . . are formed on the plural optical waveguide paths 121a, 121b, . . . respectively. While optical fibers are connected to a plurality of these optical waveguide paths, the light which is modulated by the Bragg grating portions is conducted to the beam separator 12 via an optical fiber array 43 containing a plurality of optical fibers. On the other hand, in the ultrasonic transmission unit 40, the ultrasonic transmitting element 19 is supported by a sound absorbing material (acoustic material) 24. Also, electrodes 17 and 18 connected to a conducting wire 42 are provided with this ultrasonic transmitting element 19 so as to apply a voltage to the ultrasonic transmitting element 19.

An acoustic matching layer 22 is formed among the optical waveguide path 121 containing the Bragg grating portion 122, the ultrasonic transmitting element 19, and also the housing 21 in order to improve matching effects of acoustic impedance thereof. Also, an acoustic lens material 23 is provided on the surface of the housing 21. The reason why these acoustic matching layer 22, acoustic lens material 23, sound absorbing material 24, and the like are provided is similar to that of the first embodiment of the present invention.

Figure 10A:
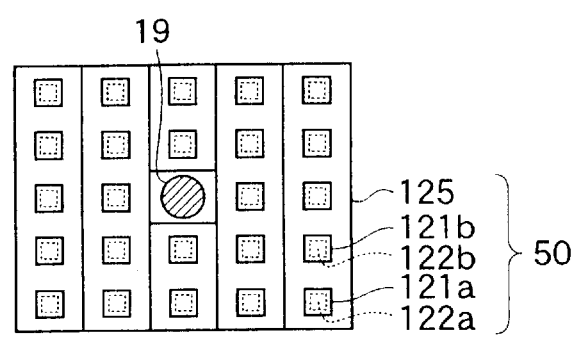
FIGS. 10A to 10D are diagrams showing partial structure of the ultrasonic probe according to the fifth embodiment of the present invention.

In this case, as represented in FIG. 10, the following four sorts of arrangements may be conceived with respect to the ultrasonic transmitting element 19 and the ultrasonic detecting unit (one-dimensional optical waveguide path array) 50 in which plural sets of optical waveguide paths 121a, 121b, . . . are arranged in the one-dimensional manner;

(1) An example of arrangement in which one ultrasonic transmitting element is arranged at a center of an optical waveguide path array:

FIG. 10A is a sectional view for illustratively showing such an arrangement example that one piece of the ultrasonic transmitting element 19 is arranged at a center of a two-dimensional optical waveguide path array in which a plurality of one-dimensional optical waveguide path arrays are arranged. In accordance with this arrangement, a transmission wave owns a non-directional characteristic.

Figure 10B:
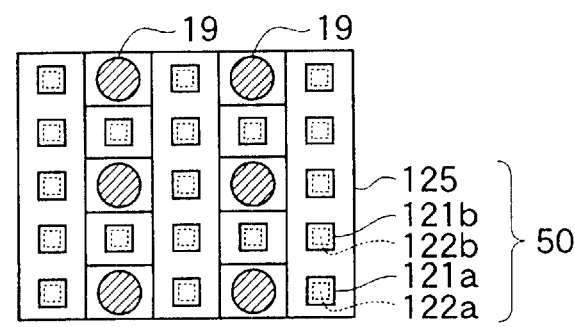

(2) Another example of arrangement in which a plurality of ultrasonic transmitting elements are arranged among a plurality of optical waveguide paths:

FIG. 10B is a sectional view for representing such an arrangement example that the ultrasonic transmitting elements 19 are alternately arranged among a plurality of optical waveguide paths containing a one-dimensional waveguide path array. Since the ultrasonic transmitting elements are arranged in the two-dimensional manner in this arrangement example, the two-dimensional beam-scanning transmission waves can be realized.

Figure 10C:
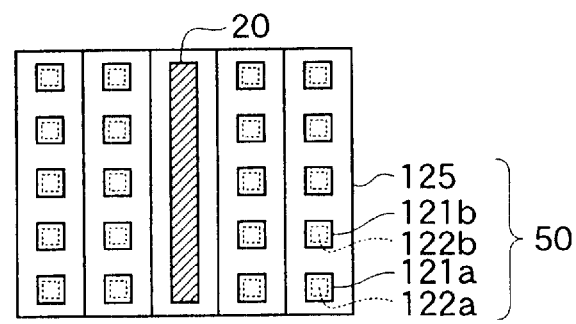

(3) Another example of arrangement in which one piece of one-dimensional ultrasonic transmitting element is arranged at a center of an optical waveguide path array:

FIG. 10C is a sectional view for illustratively showing such an arrangement example that one piece of one-dimensional ultrasonic transmission array 20 is arranged at a center of a plurality of one-dimensional optical waveguide path arrays. The one-dimensional transmission array 20 is constituted by arranging a plurality of ultrasonic transmitting elements in the one-dimensional manner. In accordance with this arrangement, one-dimensional beam-scanning transmission wave can be realized.

Figure 10D:
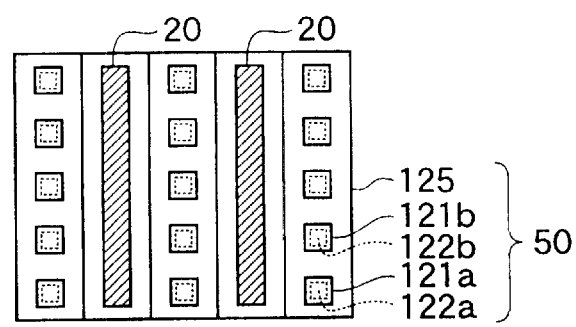

(4) Another example of arrangement in which a plurality of one-dimensional ultrasonic transmission arrays are arranged among a plurality of one-dimensional optical waveguide path arrays:

FIG. 10D is a sectional view for illustratively representing such an arrangement example that plural sets of one-dimensional ultrasonic transmission arrays 20 are alternately arranged among a plurality of one-dimensional optical waveguide path arrays 50. The one-dimensional transmission array 20 is constituted by arranging a plurality of ultrasonic transmitting elements in the one-dimensional manner. With employment of this arrangement, the two-dimensional beam scanning transmission wave can be realized.

Figure 12:
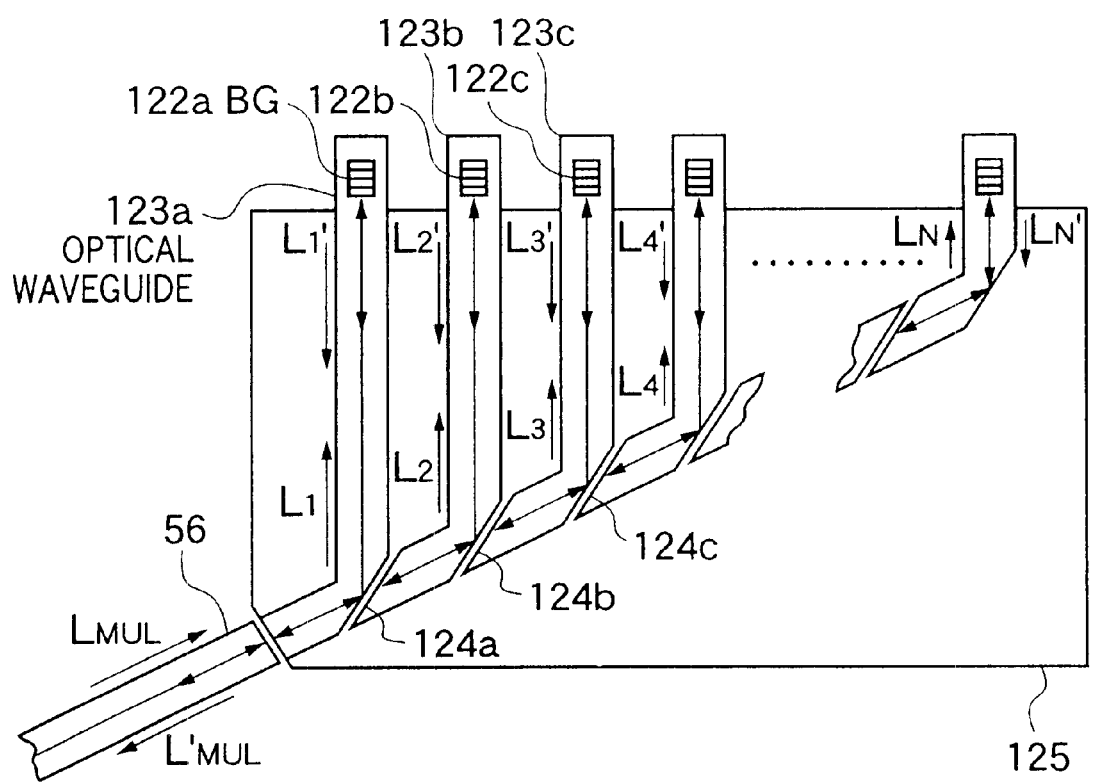
FIG. 12 is a diagram showing structure of an ultrasonic detection part as shown in FIG. 11.
Figure 13:
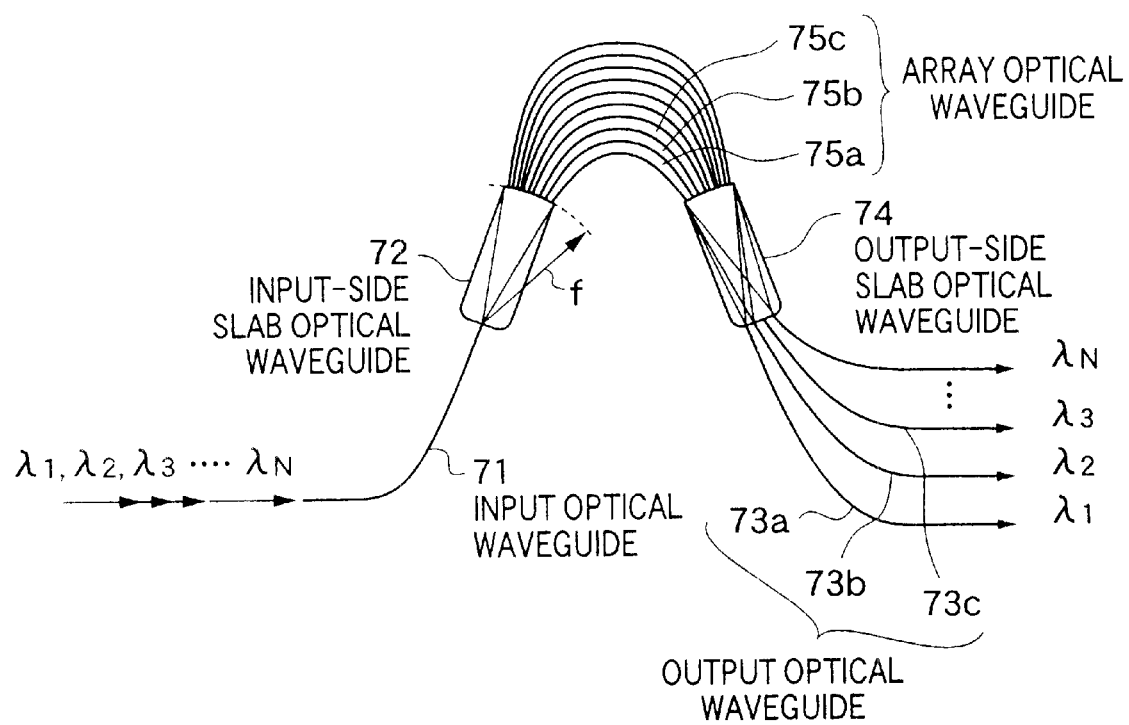
FIG. 13 is a diagram showing structure of a beam separator as shown in FIG. 11.

Next, an ultrasonic receiving apparatus according to a sixth embodiment of the present invention will now be explained with reference to FIG. 11 to FIG. 13. Similar to the fifth embodiment of the present invention, this sixth embodiment is featured by that while a plurality of optical waveguide paths 123a, 123b, . . . having Bragg grating structures are employed as an ultrasonic detecting element, a plurality of light having different wavelengths is multiplexed with each other, and then, the multiplexed light is used as detection light. FIG. 11 illustratively shows a basic idea of an arrangement of the ultrasonic receiving apparatus according to this sixth embodiment. FIG. 12 illustratively indicates a structure of an ultrasonic detecting unit 50 shown in FIG. 11. FIG. 13 illustratively represents a structure of a beam separator 112 shown in FIG. 11.

As shown in FIG. 11, this ultrasonic receiving apparatus is comprised of a light source 111, an optical circulator 113, an ultrasonic detecting unit 50, a beam separator (optical demultiplexer) 112, photodetectors 16a, 16b, . . . and optical fibers 126, 127, 128, 129a, 129b, . . . . The ultrasonic detecting unit 50 includes an optical waveguide path having a Bragg grating structure. The beam separator 112 separates detecting light which is entered from the ultrasonic detecting unit 50. The photodetectors 16a, 16b, . . . detect intensity of separated light. The optical fibers 126, 127, 128, 129a, 129b, . . . connect these units to each other. In this fifth embodiment, as the light source 111, a broad-band light source is used for producing light having a broad band (broad-band light). As the beam separator, the optical circulator 113 is used for switching a propagation direction of light in response to a light incident direction.

In FIG. 11, the light emitted from the light source 111 is entered via the optical fiber 127 into the optical circulator 113, and further is entered via the optical fiber 126 to the ultrasonic detecting unit 50.

Referring now to FIG. 12, the ultrasonic detecting unit 50 contains a plurality of optical waveguide paths 123a, 123b, . . . formed on the substrate 125. These optical waveguide paths 123a, 123b, . . . own inverted "L" shapes and also different waveguide paths from each other. These light waveguide paths 123a, 123b, . . . are arranged in such a manner that sections thereof are arranged along one column. The Bragg gratings 122a, 122b, . . . are formed on the tip portions of the respective optical waveguide paths 123a, 123b, . . .

In this sixth embodiment, a pitch of a periodic structure of each layer which constitutes each of the Bragg gratings is determined based upon the formula (2) in such a manner that a reflection wavelength characteristic is increased with respect to a specific wavelength. In other words, the pitch "d" of the periodic structure of each layer which constitutes the Bragg grating 122a is determined based upon the formula (2) in such a manner that the Bragg wavelength becomes "$\lambda_1$". Also, the pitch "d" of the periodic structure of each layer which constitutes the Bragg grating 122b is determined based upon the formula (2) in such a manner that the Bragg wavelength becomes $\lambda_2$ (being not equal to $\lambda_1$). This pitch determining method may be similarly applied to the remaining Bragg gratings 122c, 122d, . . . . As a consequence, the reflection wavelength characteristics of the Bragg gratings 122a, 122b, . . . are different from each other. When ultrasonic waves are applied to a plurality of Bragg gratings 122a, 122b, . . . these Bragg gratings are compressed along the sound pressure direction of the ultrasonic waves. As a result, the pitches "d" of the periodic structures of the respective layers which constitute the respective Bragg gratings 122a, 122b, . . . are changed, so that the respective Bragg wavelengths are varied. As a consequence, while the ultrasonic waves are received, the light which is entered into the respective Bragg gratings 122a, 122b, . . . is modulated in response to the applied ultrasonic waves. It should also be noted that in this sixth embodiment, the lengths of the Bragg grating portions formed at the tip portions of the respective optical waveguide paths may be preferably selected to be shorter than, or equal to ¾ of the wavelength of the ultrasonic wave.

A tail portion of the optical waveguide path 123a is connected to the optical fiber 126. Also, a gap 124a is formed between the tail portion of the optical waveguide path 123a and a tail portion of the optical waveguide path 123b. This gap 124a may function as a beam splitter. Similarly, another gap 124b functioning as a beam splitter is formed between the tail portion of the optical waveguide path 123b and a trail portion of the optical waveguide path 123c. This gap formation is similarly applied to the remaining optical waveguide paths 123c, 123d, . . . In this sixth embodiment, a plurality of optical waveguide paths 123a, 123b, . . . are connected in such a manner, so that a planar lightwave circuit (PLC) may be realized.

In this case, operations of the ultrasonic detecting unit 50 indicated in FIG. 12 will now be explained. When light $L_{MUL}$ containing a plurality of wavelength components ($\lambda_1$, $\lambda_2$, . . . $\lambda_N$) are supplied to this ultrasonic detecting unit 50, this light is demultiplexed every this light passes through a plurality of gaps 124a, 124b, . . . respectively. The light $L_1$ (having wavelength of $\lambda_1$) entered into the optical waveguide path 123a is reflected by the Bragg grating 122a toward the optical waveguide path 123a, and is modulated in response to the ultrasonic wave applied to this Bragg grating 122a to thereby produce light $L_1$'. The light $L_2$ (having wavelength of $\lambda_2$) entered into the optical waveguide path 123b is reflected by the Bragg grating 122b toward the optical waveguide path 123b, and is modulated in response to the ultrasonic wave applied to this Bragg grating 122b to thereby produce light $L_2$'. The above-described light process operation is similarly applied to the remaining light $L_3$ (having wavelength of $\lambda_3$), light $L_4$ (having wavelength of $\lambda_4$), . . . contained in the light $L_{MUL}$. The projection light $L_1$', $L_2$', . . . of the Bragg gratings 122a, 122b, . . . is sequentially multiplexed with each other in the corresponding gaps 124a, 124b, . . . and then, the multiplexed light is entered into the optical fiber 126.

Referring again to FIG. 11, the travel direction of light entered into the optical fiber 126 is changed by the optical circulator 113, and then, this light is entered via the optical fiber 128 to the beam separator (demultiplexer) 112. The beam separator 112 demultiplexes the light $L_{MUL}$' entered from the optical fiber 128 to produce a plurality of light $L_1$', $L_2$', . . . having predetermined wavelengths different from each other. A plurality of photodetectors 16a, 16b, . . . having the different detectable wavelength ranges are connected via the corresponding optical fibers 129a, 129b, . . . to the beam separator 112. Since a plurality of photodetectors 16a, 16b, . . . detect the light $L_1$', $L_2$', . . . which is entered from the corresponding optical fibers 129a, 129b, . . . it is possible to detect the strengths of the ultrasonic waves applied to the respective Bragg gratings 122a, 122b, . . . which are contained in the ultrasonic detecting unit 50.

Referring now to FIG. 13, in this sixth embodiment, as the demultiplexer 112, a demultiplexing circuit is employed which contains an arranged-wavelength grating (AWG) corresponding to one sort of the planar lightwave circuit (PLC). This multiplexing circuit is arranged in such a manner that a plurality of array optical waveguides 75a, 75b, . . . having a constant waveguide path difference are connected between an input-sided slab optical waveguide path 72 to which one input optical waveguide path 71 is connected, and also an output-sided slab optical waveguide path 74 to which a plurality of output optical waveguide paths 73a, 73b, . . .

The input-sided slab optical waveguide path 72 has a fan shape, while an edge portion of the input optical waveguide path 71 is located as a center of a curvature, whereas the output-sided slab optical waveguide path 74 has a fan shape, while edge portions of the plural output optical waveguide paths 73a 73b, . . . are located as a center of a curvature. A plurality of array optical waveguide paths 75a, 75b, . . . are arranged in a radial shape in such a way that the respective optical axes thereof may pass through both the curvature centers of the input-sided slab optical waveguide path 72 and the output-sided slab optical waveguide path 74. As a result, both the input-sided slab optical waveguide path 72 and the output-sided slab optical waveguide path 74 may realize such operations equivalent to a lens.

In the case that the light $L_{MUL}$' containing a plurality of wavelength components ($\lambda_1$, $\lambda_2$, . . . $\lambda_N$) is entered into the input optical waveguide path 71, this light is extended in the input-sided slab optical waveguide path 72 due to diffraction so as to excite a plurality of array optical waveguide paths 75a, 75b, . . . with in-phase condition. When the respective excitation light passes through the corresponding array optical waveguide paths 75a, 75b, . . . phase differences corresponding to the optical waveguide path differences are given to the excitation light, and thereafter the excitation light is reached to the output-sided slab optical waveguide path 74. When a plurality of light entered into the output-sided slab optical waveguide path 74 will interfere with each other because of the lens effect, the interfering light is focused onto one point on the side where a plurality of output optical waveguide paths 73a, 73b, . . . and then is diffracted in such a direction along which the in-phase condition can be satisfied. It should also be understood that in the demultiplexing circuit (beam separator) shown in FIG. 13, if the units provided on the input side are replaced by the units provided on the output side, then this demultiplexing circuit may be employed as an optical multiplexing circuit.

In this sixth embodiment, the broad-band light source has been used as the light source. Alternatively, while a plurality of laser oscillators having different wavelengths are employed, laser light emitted from these laser oscillators is multiplexed with each other to produce multiplexed laser light. Then, this multiplexed laser light may be employed as the light source. In this alternative case, the demultiplexer (beam separator) as shown in FIG. 13 may be employed as the multiplexer.

As described above, according to the present invention, it is possible to realize the two-dimensional ultrasonic probe having the transmitting function of the ultrasonic wave without electric interconnection of a numerous number of microcomponents and without the increase in crosstalk and in electric impedance. Further, according to the present invention, it is possible to realize an ultrasonic diagnosis apparatus capable of obtaining a three-dimensional image with higher quality by using the above-explained two-dimensional ultrasonic probe.

What is claimed is:

1. An ultrasonic probe comprising:
   transmitting means for transmitting an ultrasonic signal from said probe to an object; and
   receiving means for receiving an ultrasonic signal reflected from said object, said receiving means including an ultrasonic sensing part having an optical reflectance which changes in accordance with the received ultrasonic signal such that a change of the optical reflectance is detected as an amplitude modulation of a light beam reflected from said ultrasonic sensing part.

2. An ultrasonic probe according to claim 1, wherein said transmitting means is based on a piezoelectric system which generates an ultrasonic signal in accordance with an applied voltage.

3. An ultrasonic probe according to claim 1, wherein said ultrasonic sensing part has a function of transforming the ultrasonic signal to an optical signal.

4. An ultrasonic probe according to claim 1, wherein said receiving means includes an optical fiber array to which said ultrasonic sensing part is provided.

5. An ultrasonic probe according to claim 1, wherein said receiving means includes a plurality of optical waveguide paths in each of which said ultrasonic sensing part is provided.

6. An ultrasonic probe according to claim 1, wherein said receiving means includes a sensor having a Fabry-Perot resonator structure.

7. An ultrasonic probe according to claim 1, wherein said receiving means includes a sensor having a Bragg grating structure.

8. An ultrasonic probe according to claim 7, wherein the ultrasonic sensing part in said sensor having the Bragg grating structure has a length of not larger than ¾ of a wavelength of an ultrasonic wave which is propagated through said ultrasonic sensing part.

9. An ultrasonic probe according to claim 1, wherein said receiving means includes a sensor for detecting the ultrasonic signal by use of a change in amount of reflection/transmission light on a light reflection plane due to vibration of an object which exists in an evanescent field near the light reflection plane in accordance with the received ultrasonic signal.

10. An ultrasonic diagnosis apparatus comprising:
    transmitting means for transmitting an ultrasonic signal from said apparatus to an object;
    a drive signal generating circuit for generating a drive signal to be applied to said transmitting means so as to transmit the ultrasonic signal;
    receiving means for receiving an ultrasonic signal reflected from said object, said receiving means including an ultrasonic sensing part having an optical reflectance which changes in accordance with the received ultrasonic signals;
    a detector for detecting a change of the optical reflectance as an amplitude modulation of a light beam reflected from the ultrasonic sensing part of said receiving means to generate a detection signal; and
    signal processing means for processing the detection signal output from said detector.

11. An ultrasonic diagnosis apparatus according to claim 10, wherein said transmitting means is based on a piezoelectric system which generates an ultrasonic signal in accordance with an applied voltage.

12. An ultrasonic diagnosis apparatus according to claim 10, further comprising:
    control means for controlling said drive signal generating circuit and said signal processing means;
    an image processing unit for forming image signal on the basis of an output signal of said signal processing means; and
    an image display unit for displaying an image on the basis of the image signal.

13. An ultrasonic diagnosis apparatus according to claim 10, wherein said receiving means includes an optical fiber array to which said ultrasonic sensing part is provided.

14. An ultrasonic diagnosis apparatus according to claim 10, wherein said receiving means includes a plurality of optical waveguide paths in each of which said ultrasonic sensing parts is provided.

15. An ultrasonic diagnosis apparatus according to claim 10, wherein said receiving means includes a sensor having a Fabry-Perot resonator structure.

16. An ultrasonic diagnosis apparatus according to claim 10, wherein said receiving means includes a sensor having a Bragg grating structure.

17. An ultrasonic diagnosis apparatus according to claim 16, wherein the ultrasonic sensing part in said sensor having the Bragg grating structure has a length of not larger than ¾ of a wavelength of an ultrasonic wave which is propagated through said ultrasonic sensing part.

18. An ultrasonic diagnosis apparatus according to claim 10, wherein said receiving means includes a laser resonator for receiving the ultrasonic signal to change a frequency of an emission light beam and making the emission light beam incident upon an optical heterodyne interference system having different optical path lengths.

19. An ultrasonic diagnosis apparatus according to claim 10, wherein said receiving means includes a sensor for detecting the ultrasonic signal by use of a change in amount of reflection/transmission light on a light reflection plane due to vibration of an object which exists in an evanescent field near the light reflection plane in accordance with the received ultrasonic signal.

20. A diagnostic ultrasonic probe comprising:

a body;

an ultrasonic transmission structure disposed within said body and operative to generate and transmit external to said body an ultrasonic signal; and an ultrasonic receiving structure disposed within said body and operative to receive an ultrasonic signal from a location external to said body and to detect the received signals, using an ultrasonic sensing part having an optical reflectance which changes in accordance with the received ultrasonic signal such that a change of the optical reflectance is detected as an amplitude modulation of a light beam reflected from said ultrasonic sensing part.

21. An ultrasonic diagnosis apparatus for an object comprising:

an ultrasonic probe having integrally formed therein an ultrasonic signal generator that generates and transmits toward the object a first ultrasonic signal, and an ultrasonic receiver that receives a second ultrasonic signal from the object and converts the ultrasonic signal to an optical signal the receiver including an ultrasonic sensing part having an optical reflectance which changes in accordance with the second ultrasonic signal and a detector operative to detect a change of the optical reflectance as an amplitude modulation of a light beam output from the ultrasonic sensing part to generate a detection signal;

a drive signal generating circuit, coupled to said probe, and operative to generate a transmission signal for application to said ultrasonic signal generator as to provide timing for the generation and transmission of ultrasonic signals to the object;

a light detector, coupled to said probe, and operative to detect the optical signal from the ultrasonic receiver and to generate a detection signal;

signal processor, coupled to the light detector and operative to process the detection signal output from said light detector;

a timing unit operative to provide timing signals to the drive generating circuit and the signal processor, said timing signals providing timing coordination between the transmission of the first ultrasonic signal and detection of the optical signal resulting from detection of the second ultrasonic signal.

\* \* \* \* \*